United States Patent [19]

Grosz et al.

[11] Patent Number: 5,656,740
[45] Date of Patent: Aug. 12, 1997

[54] NUCLEIC ACID FRAGMENTS USEFUL IN THE DETECTION OF SALMONELLA

[75] Inventors: Ron Grosz, Wilmington, Del.; Mark Anton Jensen, West Chester, Pa.

[73] Assignee: E. I. Du Pont de Nemours and Company, Wilmington, Del.

[21] Appl. No.: 586,120

[22] Filed: Jan. 16, 1996

Related U.S. Application Data

[62] Division of Ser. No. 254,355, Jun. 6, 1994.

[51] Int. Cl.[6] .............. C12Q 1/68; C07H 21/02; C07H 21/04
[52] U.S. Cl. .............. 536/23.1; 435/6; 435/810; 436/501; 536/24.1; 536/24.3; 536/24.31; 536/24.32; 536/24.33; 935/77; 935/78
[58] Field of Search .............. 435/6, 810; 436/501; 536/23.1, 24.1, 24.3–24.33; 935/77, 78

[56] References Cited

U.S. PATENT DOCUMENTS

| | | | |
|---|---|---|---|
| 4,717,653 | 1/1988 | Webster, Jr. .............. | 435/5 |
| 5,087,558 | 2/1992 | Webster, Jr. .............. | 435/5 |
| 5,126,239 | 6/1992 | Livak et al. .............. | 435/6 |

FOREIGN PATENT DOCUMENTS

| | | | |
|---|---|---|---|
| 2 055 302 | 5/1992 | Canada .............. | C12Q 1/68 |
| 0 517 154 | 12/1992 | European Pat. Off. .............. | C12Q 1/68 |
| 0 517 361 | 12/1992 | European Pat. Off. .............. | C12Q 1/68 |
| 0 543 484 | 5/1993 | European Pat. Off. .............. | C12Q 1/68 |
| WO 90/11370 | 10/1990 | WIPO .............. | C12Q 1/68 |
| WO 90/15157 | 12/1990 | WIPO .............. | C12Q 1/68 |
| WO 92/03567 | 3/1992 | WIPO .............. | C12P 19/34 |
| WO 92/07095 | 4/1992 | WIPO .............. | C12Q 1/68 |
| WO 92/07948 | 5/1992 | WIPO .............. | C12P 19/34 |
| WO 92/14844 | 9/1992 | WIPO .............. | C12Q 1/68 |

OTHER PUBLICATIONS

Enns, R.K., *Lab. Med.*, 19(5), 295–300, 1988.
Mordarski, M., *Soc. Appl. Bacteriol. Tech. Ser.*, 20(Chem. Methods Bact. Syst.), 41–66, 1985.
Southern, E.M., *J. Mol. Biol.*, 98, 503–517, 1975.
Botstein, et al, *Am. J. Hum. Genet.*, 342, 314–331, 1980.
Williams, et al, *Nucl. Acids Res.*, 18(22), 6531–6535, 1990.
Landry, et al, *Genome*, 36, 580–587, 1993.
Van Belkum et al, *Mol. Biochem. Parasitol.*, 61, 69, 1993.
Tsen, et al, *Applied Microbiology and Biotechnology*, 35, 339–347, 1991.
Gebhardt, C. et al, *Int. Review of Cytology*, 135, 201–237, 1992.
Setlow et al. (1972) *J. of Biol. Chem*, vol. 247, No. 1, pp. 232–240.

*Primary Examiner*—Ardin H. Marschel

[57] ABSTRACT

A method is provided for the selection of diagnostic genetic markers fragments and useful in the identification of bacteria at the genus, species or serotype level. The method first involves the identification of a RAPD polymorphic DNA fragment common to a particular microbial group, the identification of the most conserved regions of that fragment, and the preparation of specific primers useful for detecting the presence of a marker within the fragment whereby that set of primers is then useful in the identification of all members of the chosen microbial group. Also provided is a specific diagnostic marker for Salmonella and primers directed thereto.

2 Claims, 5 Drawing Sheets

FIG.2

```
  1  TTAGTCACGGCAGCCGCGAGGATGATATGGATGTTAGCCGGGACGCTTAATGCGGTTAAC   60
     ----------+----------+----------+----------+----------+----------+
     AATCAGTGCCGTCGGCGCTCCTACTATACCTACAATCGGCCCTGCGAATTACGCCAATTG

61  GCCATGCCGACACCAGCGCCCGCCAGCGTGCCGAAACTGTAGAAACCATGCATCATCGGC  120
     ----------+----------+----------+----------+----------+----------+
     CGGTACGGCTGTGGTCGCGGGCGGTCGCACGGCTTTGACATCTTTGGTACGTAGTAGCCG

121  AGAACGGTTTTATTCAGCTCGCGTTCGACCGCCGCGCCTTCGACATTAATCGCCACTTCG  180
     ----------+----------+----------+----------+----------+----------+
     TCTTGCCAAAATAAGTCGAGCGCAAGCTGGCGGCGCGGAAGCTGTAATTAGCGGTGAAGC

181  GCGGCGCCAAAACTGGCGCCGAAAACGGCTAATCCAAGGGCAAAAATCAGCGGCGAGGCG  240
     ----------+----------+----------+----------+----------+----------+
     CGCCGCGGTTTTGACCGCGGCTTTTGCCGATTAGGTTCCCGTTTTTAGTCGCCGCTCCGC

241  CACCACAGCGCGACGCTAAGAATAACCATCCCGGTTACTGCACAGGTCATCGTCGTGCGA  300
     ----------+----------+----------+----------+----------+----------+
     GTGGTGTCGCGCTGCGATTCTTATTGGTAGGGCCAATGACGTGTCCAGTAGCAGCACGCT

301  ATAACCTTCCGGGTGCCAAATCGTTTCACCAGCCAGGCGGAACAAAGAATACCGCTCATT  360
     ----------+----------+----------+----------+----------+----------+
     TATTGGAAGGCCCACGGTTTAGCAAAGTGGTCGGTCCGCCTTGTTTCTTATGGCGAGTAA

361  GAACCGATAGAAAGCCCGAATAAGACCGCCCCCATTTCCGCGGTAGAGACGGAAAGAATA  420
     ----------+----------+----------+----------+----------+----------+
     CTTGGCTATCTTTCGGGCTTATTCTGGCGGGGGTAAAGGCGCCATCTCTGCCTTTCTTAT

421  TCCCGAATAGCAGGCGTTCGGGTTGCCCAGGAGGCCATCAGCAGTCCGGGTAAAAAGAAG  480
     ----------+----------+----------+----------+----------+----------+
     AGGGCTTATCGTCCGCAAGCCCAACGGGTCCTCCGGTAGTCGTCAGGCCCATTTTTCTTC

481  AACATAAACAGCGCCCAGGTACGGCGTTTTAAGGCGTTACGTGAGGAGAGGACGGTCATA  540
     ----------+----------+----------+----------+----------+----------+
     TTGTATTTGTCGCGGGTCCATGCCGCAAAATTCCGCAATGCACTCCTCTCCTGCCAGTAT

541  GCGTCAGGCCAGAAAATAGAAGCGAGAGGTAAACATTAGCAAGCTTGTGTACATTTGTAC  600
     ----------+----------+----------+----------+----------+----------+
     CGCAGTCCGGTCTTTTATCTTCGCTCTCCATTTGTAATCGTTCGAACACATGTAAACATG

601  ATATCATCGTCATACTTCATTGTGCAGACAGTTTTTACTGTCTGTTTTTTCAGCGTAAGC  660
     ----------+----------+----------+----------+----------+----------+
     TATAGTAGCAGTATGAAGTAACACGTCTGTCAAAAATGACAGACAAAAAGTCGCATTCG

661  GGCAGGCTACTATCGCCTGCATCCTGAATGAGATGTGGAACTCATCATGAAAGAAAATGC  720
     ----------+----------+----------+----------+----------+----------+
     CCGTCCGATGATAGCGGACGTAGGACTTACTCTACACCTTGAGTAGTACTTTCTTTTACG

721  CGTAAGCGCGCCAATGATCCTAAGCGACGGGAAAAAATAATTCAGGCCACACTGGAAGCG  780
     ----------+----------+----------+----------+----------+----------+
     GCATTCGCGCGGTTACTAGGATTCGCTGCCCTTTTTTATTAAGTCCGGTGTGACCTTCGC

781  GTAAAGACCTATGGCACTCTGCCGTGACTAA   811    (SEQ ID NO.:1)
     ----------+----------+----------+-
     CATTTCTGGATACCGTGAGACGGCACTGATT         (SEQ ID NO.:20)
```

FIG.3
PRIMERS
54-23/665rc-23
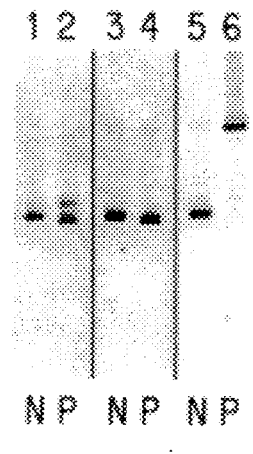
126-23/648rc-23

NUCLEIC ACID FRAGMENTS USEFUL IN THE DETECTION OF SALMONELLA

This is a division of application Ser. No. 08/254,355, filed Jun. 6, 1994.

FIELD OF INVENTION

The invention relates to the field of molecular biology and the use of randomly amplified nucleic acid fragments for the selection of genetic markers useful in the identification of bacteria at the genus, species or serotype level. This invention further relates to a specific DNA marker sequence useful for the detection of Salmonella, and use of that diagnostic marker to determine if an unknown bacterium is a member of the genus Salmonella.

BACKGROUND

An integral aspect of the field of microbiology is the ability to positively identify microorganisms at the level of genus, species or serotype. Correct identification is not only an essential tool in the laboratory but plays a significant role in the control of microbial contamination in the processing of food stuffs, production of agricultural products and monitoring of environmental media such as ground water. Increasing stringency in regulations which apply to microbial contamination have resulted in a corresponding increase in industry resources which must be dedicated to contamination monitoring.

Of greatest concern is the detection and control of pathogenic microorganisms. Although a broad range of microorganisms have been classified as pathogenic, attention has primarily focused on a few bacterial groupings such as Escherichia, Salmonella, Listerin and Clostridia. Typically, pathogen identification has relied on methods for distinguishing phenotypic aspects such as growth or motility characteristics, and immunlogical and serological characteristics. Selective growth procedures and immunological methods are the traditional methods of choice for bacterial identification, and can be effective for the presumptive detection of a large number of species within a particular genus. However, these methods are time consuming, and are subject to error. Selective growth methods require culturing and subculturing in selective media, followed by subjective analysis by an experienced investigator. Immunological detection (e.g., ELISA) is more rapid and specific, however it still requires growth of a significant population of organisms and isolation of the relevant antigens. For these reasons interest has turned to detection of bacterial pathogens on the basis of nucleic acid sequence.

It is well known, for example, that nucleic acid sequences associated with the ribosomes of bacteria are often highly conserved across genera and are therefore useful for identification (Webster, U.S. Pat. Nos. 4,717,653 and 5,087,558; Enns, Russel K. Lab. Med., 19, 295, (1998); Mordarski, M. Soc. Appl. Bacteriol. Tech. Ser., 20 (Chem. Methods Bact. Syst.), 41, (1985)). Weisburg et al., (EP 51736) disclose a method for the detection and identification of pathogenic microorganisms involving the PCR amplification and labeling of a target nucleotide for hybridization to 16S rDNA of E. coli and Lane et al., (WO 9015157) teach universal nucleic acid probes that hybridize to conserved regions of 23S or 16S rRNA of eubacteria.

Although bacterial ribosomal nucleic acids contain highly conserved sequences, they are not the only sources of base sequence conservation that is useful for microorganism identification. Wheatcroft et al., (CA 2055302) describe the selection of transposable elements, flanked by unique DNA sequences for the detection of various Rhizobium strains. Similarly Tommassen et al., (WO 9011370) disclose polynucleotide probes and methods for the identification and detection of gram-positive bacteria. The method of Tommassen et al., relies on probes corresponding to relatively short fragments of the outer membrane protein OmpA, known to be highly conserved throughout gram-positive genera. Atlas et al., (EP 517154) teach a nucleic acid hybridization method for the detection of Giardia sp. based on designing probes with sequences complementary to regions of the gene encoding the giardin protein. Webster, J. A., (U.S. Pat. No. 4,717,653) has expanded upon the use of rRNA in disclosing a method for the characterization of bacteria based on the comparison of the chromatographic pattern of restriction endonuclease-digested DNA from the unknown organism with equivalent chromatographic patterns of at least 2 known different organism species. The digested DNA has been hybridized or reassociated with ribosomal RNA information-containing nucleic acid from, or derived from a known probe organism. The method of Webster et al., effectively establishes a unique bacterial nucleic acid "fingerprint" corresponding to a particular bacterial genus against which unknown "fingerprints" are compared.

The methods described above are useful for the detection of bacteria but each relies upon knowledge of a gene, protein, or other specific sequence known a priori to be highly conserved throughout a specific bacterial group. An alternative method would involve a nontargeted analysis of bacterial genomic DNA for specific non-phenotypic genetic markers common to all species of that bacteria. For example, genetic markers based on single point mutations may be detected by differentiating DNA banding patterns from restriction enzyme analysis. As restriction enzymes cut DNA at specific sequences, a point mutation within this site results in the loss or gain of a recognition site, giving rise in that region to restriction fragments of different length. Mutations caused by the insertion, deletion or inversion of DNA stretches will also lead to a length variation of DNA restriction fragments. Genomic restriction fragments of different lengths between genotypes can be detected on Southern blots (Southern, E. M., J. Mol. Biol. 98, 503, (1975). The genomic DNA is typically digested with any restriction enzyme of choice, the fragments are electrophoretically separated, and then hybridized against a suitably labelled probe for detection. The sequence variation detected by this method is known as restriction length polymorphism or RFLP (Botstein et al. Am. J. Hum. Genet. 342, 314, (1980)). RFLP genetic markers are particularly useful in detecting genetic variation in phenotypically silent mutations and serve as highly accurate diagnostic tools.

Another method of identifying genetic polymorphic markers employs DNA amplification using short primers of arbitrary sequence. These primers have been termed 'random amplified polymorphic DNA', or "RAPD" primers, Williams et al., Nucl. Acids. Res., 18, 6531 (1990) and U.S. Pat. No. 5,126,239; (also EP 0 543 484 A2, WO 92/07095, WO 92/07948, WO 92/14844, and WO 92/03567). The RAPD method amplifies either double or single stranded nontargeted, arbitrary DNA sequences using standard amplification buffers, dATP, dCTP, dGTP and TTP and a thermostable DNA polymerase such as Taq. The nucleotide sequence of the primers is typically about 9 to 13 bases in length, between 50 and 80% G+C in composition and contains no palindromic sequences. RAPD detection of genetic polymorphisms represents an advance over RFLP in that it is less time consuming, more informative, and readily susceptible to automation. Because of its sensitivity for the detection of polymorphisms RAPD analysis and variations based on RAPD/PCR methods have become the methods of choice for analyzing genetic variation within species or closely related genera, both in the animal and plant kingdoms. For example, Landry et al., (*Genome*, 36, 580, (1993)) discuss the use of RAPD analysis to distinguish various species of minute parasitic wasps which are not morphologically distinct. Van Belkum et al., (*Mol. Biochem Parasitol* 61, 69, (1993)) teach the use of PCR-RAPD for the distinction of various species of Giardi.

In commonly assigned application U.S. Ser. No. 07/990, 297, Applicants disclose a method of double-nested PCR which is used to detect the presence of a specific microbe. This disclosure first describes identifying a random unique segment of DNA for each individual microorganism which will be diagnostic for that microorganism. To identify and obtain this diagnostic nucleic acid segment a series of polymorphic markers is generated from each organism of interest using single primer RAPD analysis. The RAPD series from each organism is compared to similarly generated RAPD series for other organisms, and a RAPD marker unique to all members of the group is then selected. The unique marker is then isolated, amplified and sequenced. Outer primers and inner primers suitable for double-nested PCR of each marker may then be developed. These primers comprise sequence segments within the RAPD markers, wherein the inner set of primers will be complementary to the 3' ends of the target piece of nucleic acid. These nested primers may then be used for nested PCR amplification to definitely detect the presence of a specific microorganism.

In the present method Applicants have more particularly adapted and more fully described this RAPD methodology to identify a sequence, or marker; the presence of which will be diagnostic for all individuals of a genetically related population. The present method first involves a RAPD amplification of genomic DNA of a representative number of individuals within a specific genus, species or subspecies to produce a RAPD amplification product, termed the diagnostic fragment. This diagnostic fragment must be present in the RAPD profiles in over 90% of the individuals tested. Sequence information from the diagnostic fragment will then enable identification of the most suitable PCR primer binding sites within the diagnostic fragment to define a unique diagnostic marker. Primers flanking this marker will be useful to produce an amplification product in the genetically selected group, but will not produce any amplification product in individuals outside of that group.

An important aspect of the present invention is the identification of the most conserved primer binding sites within this diagnostic sequence, which is accomplished by first determining which individuals, in the genus or grouping to be detected, exhibit the most genetic variation within the diagnostic sequence. Screening this subpopulation of "most polymorphic" individuals using various primers generated from the diagnostic sequence will define the most highly conserved primer bindings sites within the diagnostic fragment. Primers directed toward these highly conserved primer binding sites are then useful for the detection of all members of the genus, based upon the ability of the selected primers to amplify the diagnostic marker present in that particular population. A "yes" or "no" answer can then be readily provided to the question of whether a microorganism is a member of the genetically related population. If DNA amplification occurs using these primers, the target is present and the identity is confirmed as "yes". If amplification does not occur, the answer is no; the microorganism is not a member of that genetically related population. The necessity of electrophoresis to determine the presence of a marker of any particular size is eliminated.

Applicants' method is distinctive in that to accomplish detection of a member of a group of organisms, the method first relies on determining the most conserved regions of a diagnostic fragment from a phenotypically uncharacterized segment of DNA common to all members of that group. One of skill in the art will recognize that conservation of sequence may represent both an ally and an enemy in the process of identification of the members of a particular genus. For example, many bacterial sequences are conserved across genera and hence would not be useful in the determination of species within a particular genus. It is precisely for that reason that methods heretofore elucidated in that art rely primarily on the analysis of sequences derived from proteins or genes known to be specific to a particular genus, i.e., ribosomal RNA or outer membrane proteins. Applicants' method departs from the art in that the conserved sequences of the instant method are not derived from a known gene, nor is the sequence associated with any known phenotypic characteristic. Further, Applicants' method is refined by the selection of the most conserved region of the diagnostic fragment by comparison with the genomic DNA of a subpopulation of individuals exhibiting the most genetic variation within the diagnostic fragment. Applicants' method presupposes that the regions of the diagnostic fragment most conserved within the polymorphic subpopulation will also be conserved within the larger population comprising all members of the genus. Applicants are unaware of any art teaching this supposition.

The process of the present invention has been enabled in the present disclosure by the elucidation of a diagnostic marker sequence which is useful in rapidly and definitively identifying bacteria from the genus Salmonella.

SUMMARY OF THE INVENTION

The present invention provides a method for the determination of diagnostic genetic markers for the identification of individuals of a genetically related population of microorganisms. The method comprises the following steps:

(i) The first step entails performing a RAPD amplification on the genomic DNA of a representative number of individuals from a genetically related population, wherein said number of individuals will comprise the positive test panel, and whereby the RAPD amplification performed on individuals of the positive test panel will generate a RAPD marker profile from each individual of the positive test panel. Similarly the same RAPD amplification is performed On the genomic DNA of a significant number of individuals genetically unrelated to the positive test panel, wherein said number of genetically unrelated individuals will comprise the negative test panel, and whereby the RAPD amplification en individuals of the negative test panel will generate a RAPD marker profile from each individual of the negative test panel.

(ii) The second step comprises comparing the RAPD marker profiles from individuals of the positive test panel with the RAPD marker profiles from individuals of the negative test panel and thereby selecting a diagnostic nucleic acid fragment wherein said fragment is present in over 90% of the RAPD marker profiles from the positive test panel and absent in the RAPD marker profiles from the negative test panel.

(iii) The nucleotide sequence of said diagnostic fragment is determined to identify available primer binding sites.

(iv) One or more pairs of primers corresponding to the available primer binding sites of step (iii) are prepared.

(v) Primer-directed amplification is performed on the genomic DNA of a significant number of individuals from the positive test panel using the primer pairs of step (iv), whereby a subpopulation of individuals which are the most polymorphic with respect to said diagnostic fragment is identified.

(vi) Primer-directed amplification is next performed on the genomic DNA of said polymorphic subpopulation of (v) using several candidate primer pairs derived from the sequence of said diagnostic fragment,. whereby a particular candidate primer pair which produces primer amplification product for the highest percentage of individuals within the polymorphic subpopulation is thereby empirically selected. This primer pair now defines the diagnostic marker for that genetically related population of step (i).

(vii) The method further comprises the step of confirming that the particular primer pair identified in (vi) is useful for amplifying a diagnostic genetic marker which is present in all of the genetically related individuals while absent in all of the genetically unrelated individuals, wherein said confirmation is accomplished by amplifying the genomic DNA of all individuals of the positive and negative test panels with said particular primer pair to determine that said primer pair is effective in amplifying a diagnostic genetic marker in all individuals of the positive test panel and is ineffective in amplifying said diagnostic marker in all individuals of the negative test panel.

This invention further provides a method of determining whether an unknown bacterium is a member of the genus Salmonella, comprising analyzing the genomic DNA of said unknown bacterium to detect the presence of nucleic acid Sequence ID No. 1 or its complement, No. 20. In a preferred embodiment, said analysis can be accomplished by amplification using the primer pairs of Sequence ID Nos. 15 and 19.

This invention further provides isolated nucleic acid fragments having Sequence ID Nos. 1, 4, 14, 15, 16, 17, 18, 19, 10, 21 and 22.

BRIEF DESCRIPTION OF THE FIGURES

FIG. 2 shows the sequence of an 811 bp Salmonella diagnostic nucleic acid fragment, Sequence ID No. 1, which was generated by amplification of genomic DNA isolated from *Salmonella typhimurium* (ATCC 29057) with the single 12-base primer 12CN03. The complementary strand to Sequence ID No. 1 is Sequence ID No. 20. Within this 811 bp nucleic acid of FIG. 2, at position No. 35 to 786, is Sequence ID No. 21 and its complement, Sequence ID No. 22, which comprise the diagnostic marker of the invention for Salmonella.

FIG. 2 also includes the following sequences within SEQ ID NO.:1: SEQ ID NO.:14 (at bp 34–59) and SEQ ID NO.:15 (at bp 35–60). FIG. 2 also includes the following sequences within SEQ ID NO.:20: SEQ ID NO.:16 (at bp 253–278), SEQ ID NO.:17 (at bp 251–276), SEQ ID NO.:18 (at bp 122–147), and SEQ ID NO.:19 (at bp 26–52).

FIG. 3 is a composite photograph showing normal (N) and polymorphic (P) electrophoretic PCR amplification products generated from the primers 54-23/665rc-23 (Sequence ID Nos. 10/13) and primers 126-23/648rc-23 (Sequence ID Nos. 11/12) from a variety of Salmonella strains.

DETAILED DESCRIPTION OF THE INVENTION

Figure 1A:
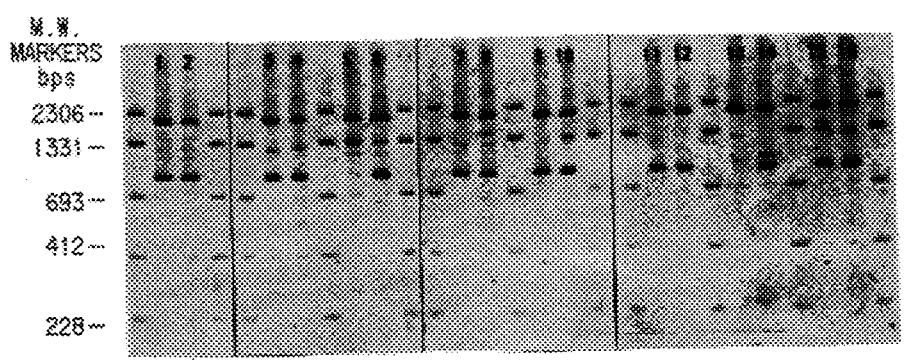
FIG. 1A is a composite photograph showing electrophoretic marker profiles of amplification products for the positive test panel of Salmonella strains amplified with a single RAPD primer, 12CN03 (Sequence ID No. 4).

As used herein the following terms may be used for interpretation of the claims and specification.

"Nucleic acid" refers to a molecule which can be single stranded or double stranded, comprising monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The term "primer-directed amplification" refers to any of a number of methods known in the art that result in logarithmic amplification of nucleic acid molecules using the recognition of a specific nucleic acid sequence or sequences to initiate an amplification process. Applicants contemplate that amplification may be accomplished by any of several schemes known in this art, including but not limited to the polymerase chain reaction (PCR) or ligase chain reaction (LCR). If PCR methodology is selected, the amplification method would include a replication composition consisting of for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.).

A "diagnostic fragment" refers to a particular DNA sequence which is highly conserved amongst the individuals of a particular genetically related population, for example, a genus, species, or subspecies of bacteria. In the instant invention, the term "diagnostic fragment" is used to refer to that fragment generated during RAPD amplification which is present in the RAPD profiles from a particular related group but absent in profiles from individuals outside of that group. The term "diagnostic marker" is used herein to refer to that portion of the diagnostic fragment which can be targeted to produce an amplification product in only members of the related group. The diagnostic marker is not present outside the related group, and attempts to amplify the diagnostic markers in individuals outside of the related group will result in no nucleic acid being amplified.

The term "primer" refers to a nucleic acid fragment or sequence that is complementary to at least one section along a strand of the sample nucleic acid, wherein the purpose of the primer is to sponsor and direct nucleic acid replication of a portion of the sample nucleic acid along that string. Primers can be designed to be complementary to specific segments of a targeted sequence. In PCR, for example, each primer is used in combination with another primer forming a "primer set" or "primer pair", this pair flanks the targeted sequence to be amplified. In RAPD amplification, single arbitrary primers are used to amplify nontargeted segments of nucleic acid which are located between the primer sequence sites in opposing DNA strands. The term "primer", as such, is used generally herein by Applicants to encompass any sequence-binding oligonucleotide which functions to initiate the nucleic acid replication process. "Diagnostic primers" will refer to primers designed with sequences complementary to primer binding sites on diagnostic marker. Diagnostic primers are useful in the convenient detection and identification of individuals of a genetically related population.

A genetically related population refers to any grouping of microorganisms possessing multiple or single phenotypic characteristics of sufficient similarity to allow said organisms to be classified as a single genus, species, or subspecies of bacteria. For purposes of the present disclosure, examples of genetically related populations include, for example, the genus Salmonella or the species *Listeria monocytogenus*.

A "test panel" refers to a particular group of organisms or individuals selected on the basis of their genetic similarity to each other, or their genetic dissimilarity to another group (i.e., another genus, species, subspecies). A "positive test panel" will refer to a number of individuals selected for the desired genetic similarity between those individuals, and in the instant case will be comprised of individuals included within the desired genetically related population. Examples of a positive test panel would be, for example, representative members of all the species of a particular genus (assuming that genus is the desired 'genetically related population'). Similarly, a "negative test panel" will refer to a test panel selected on the basis of genetic diversity between its members and the members of the positive test panel. An example of a negative test panel when the positive test panel is bacteria of the genus Salmonella, would be bacteria and other organisms outside of the Salmonella genus.

The term "representative number of individuals" refers to individuals within a genetically related population which are selected such that they represent the widest possible range of biochemical, morphological and immunological attributes known to exist within the targeted genetically related population. The term "representative number of individuals", when referring to individuals genetically unrelated to the genetically related population (the negative test panel), means those microorganisms which are not included within the genetically related group but are genetically similar to that group.

The term "unknown bacterium" refers to a bacterium whose identity is unknown.

The term "derived from", with reference to an amplification primer, refers to the fact that the sequence of the primer is a fragment of the sequence from which it has been "derived". The fragment is always denoted in a 5' to 3' orientation. The useful primer sequence size range for PCR amplification is about 15 base pairs to about 30 base pairs in length.

The term "RAPD" refers to 'random amplified polymorphic DNA'. "RAPD amplification" refers to a method of single primer directed amplification of nucleic acids using short primers of arbitrary sequence to amplify nontargeted, random segments of nucleic acid. U.S. Pat. No. 5,126,239. "RAPD method" or "RAPD analysis" refers to a method for the detection of genetic polymorphisms involving the nontargeted amplification of nucleic acids using short primers of arbitrary sequence, whereby the profile or pattern of 'RAPD' amplification products is compared between samples to detect polymorphisms. "RAPD primers" refers to primers of about 8 to 13 bp, of arbitrary sequence, useful in the RAPD amplification or RAPD analysis according to the instant method. The "RAPD marker profile" refers to the pattern, or fingerprint, of amplified DNA fragments which are amplified during the RAPD method and separated and visualized by gel electrophoresis.

The diagnostic marker of the invention, once identified, can be used to identify an unknown microorganism by any of several analysis methods. In the present invention, primers flanking the marker are useful to amplify the marker using PCR. Alternatively, nucleic acid probes could be developed based upon some or all of the diagnostic marker sequences and thus used to detect the presence of the marker sequence using standard hybridization and reporter methods. It is contemplated that regions of about 30 base pairs or more of the diagnostic marker, especially encompassing the primer regions could be used as sites for hybridization of diagnostic probes.

The present invention provides a method for the determination of genetic markers useful in the detection and identification of all members of a genetically related population. Examples of genetically related populations include following:

1) microorganisms belonging to the genus Salmonella
2) microorganisms belonging to the species *Listeria monocytogenes*
3) microorganisms belonging to the serotype of *Escherichia coli* designated 0157:H7.

The instant method is particularly useful for the detection of specific genera, species or subspecies of bacteria which may be present either in food, human or animal body fluids or tissues, environmental media or medical products and apparatti.

To practice the instant method, a RAPD amplification, using a short arbitrary primer, is performed on the genomic DNA of at least 30 individuals from a genetically related population. These individuals are selected such that they represent the widest possible range of biochemical, morphological and immunological attributes known to exist within the targeted genetically related population. The electrophoretically resolved patterns of amplification products produced by the RAPD amplifications are then compared, in hopes of indentifying a distinctive RAPD amplification product which is present in over 90% of the individuals tested. If this product is not found when the same RAPD amplification is then performed on the genomic DNA of at least 30 strains of microorganisms which fall outside of the targeted population, then this fragment is deemed to be suitable diagnostic fragment and it is then sequenced to determine suitable primer binding sites for further analysis and primer generation. It is imperative that the most conserved regions of the diagnostic fragment be determined for the generation of useful diagnostic primers, i.e., primers which will be capable of producing an amplification product in all members of the genetically related group. Determination of the most conserved region is accomplished by first determining which individuals, in the population group to be detected, exhibit the most genetic variation within the diagnostic fragment sequence. The genomic DNA of this polymorphic subpopulation is then analyzed with several sets of PCR primers generated from the diagnostic fragment to define the most highly conserved PCR primer bindings sites within the diagnostic fragment. Primers generated from these highly conserved primer binding sites are then used in assay methods for the detection of all members of the genus. The method is more particularly described below with reference to the specific method steps as provided in the Summary of the Invention.

Selection of RAPD primers and detection of diagnostic fragment in members of the positive and negative control panels, steps (i) and (ii):

Genomic DNA isolated from positive and negative test panels of microorganisms was subjected to RAPD amplification using eight 12-base primers of arbitrary sequence. The positive test panel comprised 62 Salmonella serotypes and is described in detail in the GENERAL METHODS section below. The negative test panel consisted of a variety of 11 non-Salmonella species and is also described in the GENERAL METHODS section below. Techniques for the isolation of genomic DNA are common and well known in the art and examples may be found in Sambrook et al., Molecular Cloning: A Laboratory Manual—volumes 1,2,3 (Cold Spring Harbor Laboratory: Cold Spring Harbor, N.Y.

RAPD primers of 12 bases in length were used because at this primer length the RAPD patterns generally contained one to five amplified DNA fragments. Use of shorter primers frequently resulted in a large number of amplification products, which made the extraction of a single homogeneous fragment for sequencing much more difficult. When primers of greater than 12 bases were used a significant fraction of the bacterial strains produced no RAPD products which would have necessitated the screening of a much larger number of arbitrary primers. One of the primers, designated 12CN03, was found to produce both an 800 bp and 2000 bp amplification product in over 90% of the positive test panel. 12CN03 had the sequence of TTA GTC ACG GCA (Sequence ID No. 4). Neither the 800 bp nor 2000 bp fragment was seen in the amplification products of the negative test panel with primer 12CN03. Because of its shorter length it was decided to focus attention on the 800 bp fragment for further analysis and this became the Salmonella diagnostic fragment. FIG. 2 shows this fragment, wherein the top strand is shown as Sequence ID No. 1, and its complementary strand is shown as Sequence ID No. 20.

The 800 bp fragment did not appear with equal intensity in all of the Salmonella strains in the positive test panel. Considering the extreme sensitivity of RAPD patterns to sequence polymorphisms, it is assumed that the variations in the intensity of the RAPD marker in some Salmonella strains was the result of a minor sequence variation in the vicinity of the primer site. Considering the frequency at which the Salmonella fragment appeared, it could still be possible for highly conserved sequences, which are common to all members of the genus Salmonella, to be found between the 12CN03 priming sites flanking the 800 bp fragment.

Sequencing of diagnostic fragment, step (iii):

The 800 bp product for *Salmonella typhimurium* 587 (ATCC #29057) was selected for extraction and sequencing. This strain was selected because it is a well-characterized type strain and because this serotype of Salmonella is a frequently encountered pathogenic microorganism. The amplification product was isolated by gel electrophoresis and the fragment was cut from the gel, eluted and reamplified with the 12CN03 primer to provide quantities of DNA suitable for sequencing. Sequencing was accomplished using the chain-termination method of Sanger et al. (*Proc. Natl. Acad. Sci. USA* 74, 5463, (1977)) using fluorescence-labeled dideoxynucleotides and the Genesis 2000™ DNA Analysis System (E. I. du Pont de Nemours and Company, Wilmington, Del.). The complete sequence of the 800 bp Salmonella diagnostic fragment is shown in FIG. 2.

Identification of the most highly conserved regions of the diagnostic fragment. steps (iv) and (v):

In order for the Salmonella diagnostic fragment to be useful for the detection of all members of the Salmonella genus, it is necessary to identify the most conserved regions (i.e., primer sites) of the diagnostic fragment. In theory, identification of the conserved regions could be accomplished by generating primers to the fragment based on the known sequence and isolating and sequencing the same fragment from all members of the Salmonella genus. Sequencing, alignment and comparison of all the sequences would allow for the determination of the most conserved portion of the sequence. Although, this approach is theoretically possible, in reality it is prohibitively time consuming and expensive. The development of a general method requires an alternate approach.

The instant method provides a more direct and rapid method of identifying the most conserved regions of the diagnostic fragment, wherein the first step is the identification of a subpopulation of Salmonella sp. which show the greatest overall variation within the 800 bp diagnostic fragment. The strains which constitute this subpopulation are referred to as "polymorphic" Salmonella. It must be understood that this subpopulation is defined as polymorphic only in the context of the diagnostic nucleic acid fragment shown in FIG. 2 and not with respect to the classical biochemical and morphological attributes, which are commonly used to classify species. Once the members of the positive test panel that are polymorphic have been identified, these polymorphic Salmonella are used to screen for the most highly conserved regions of the diagnostic fragment. This approach presumed that the priming sites that are conserved among the most polymorphic Salmonella are also conserved in the general population of Salmonella.

In order to determine which Salmonella were "polymorphic" two sets of amplification primer pairs were arbitrarily selected from the diagnostic fragment and amplifications were carried out on DNA isolated from 740 strains of Salmonella representing all six subgenus groups for each of the primer sets. The initial primer sets were selected to achieve a GC content of 55±3% for two pairs of primers all of which are located within 200 bases of the CN03 priming sites. Any strain of Salmonella which showed an amplification polymorphism was classified as a "polymorphic" Salmonella. The following amplification events were regarded as polymorphic when they occurred with either primer set:

i) weak, inconsistent, or total lack of production of an amplification product ii) amplification products which are larger or smaller than the generally observed amplification product iii) the presence of more than one amplification product.

The largest single polymorphic group among the 740 strains of Salmonella were those which produced no amplification product with at least one of the primer pairs. However, a number of strains produced either multiple amplification products or products of a different size. Some examples of these types of polymorphic amplification events are shown in FIG. 3. From the original group of 740 Salmonella strains a group of 43 polymorphic Salmonella were selected.

Selection of a diagnostic primer pair to amplify the diagnostic genetic marker, step (vi):

Once the subpopulation of "polymorphic" Salmonella was identified primers were prepared for a large number sites at both ends of the Salmonella fragment sequence. The initial criteria for primer selection was that the GC content of the two primers should match and that the overall GC content fell in the range of 55±3%. The second criteria was that the pairs of primers were all located within 200 bases of the CN03 priming sites. Using these primers amplifications were carried out on genomic DNA from the polymorphic Salmonella. Primer combinations which produced an amplification product in over 90% of the polymorphic Salmonella were selected for further evaluation. In such combinations, one of the primer sites was "locked" while the second priming site was moved upstream or downstream one base at a time. In this way the priming site that found the highest portion of polymorphic Salmonella was identified and fixed. The second priming site was then "locked" and additional primers were prepared, which moved the first priming site at the other end of the Salmonella target sequence upstream or downstream one base at a time. When the priming sites which produced an amplification product for the highest percentage of polymorphic Salmonella were identified, these primers were then evaluated for the entire test panel of Salmonella strains. Based on this analysis four regions were identified as being most conserved. Within these conserved regions five primer-pair combinations were capable of producing an amplification product in ≧95% of the polymorphic Salmonella. These primer combinations were selected for further testing.

Confirmation of selected primer pair as a diagnostic genetic marker, step (viii):

The selected priming sites were understood to be highly conserved among the "polymorphic" Salmonella. The initial step in the final screening procedure was the determination of which, if any, priming sequences were conserved outside the genus Salmonella. The selectivity of the Salmonella primer sets was evaluated using a negative test panel consisting of over 100 strains representing 28 species which were either similar phenotypically to Salmonella or likely to be found in similar environments. The primer combination which showed the lowest rate of false positive responses in the negative test panel was then evaluated to determine its inclusivity for a positive test panel consisting of over 1480 Salmonella strains.

EXAMPLES

GENERAL METHODS

Suitable methods of genetic engineering employed herein are described in Sambrook et al., Molecular Cloning: A Laboratory Manual—volumes 1,2,3 (Cold Spring Harbor Laboratory: Cold Spring Harbor, N.Y., (1989), and in the instructions accompanying commercially available kits for genetic engineering. GeneClean (Bio101 LaJolla, Calif.) was used to isolate nucleic acid fragments from agarose gels and to remove enzymes from restriction digests and was performed as specified by the manufacturer. Unless otherwise specified all other standard reagents and solutions used in the following examples were supplied by J. T. Baker Co. (Phillipsburg, N.J.).

Construction of Positive and NeGative Test Panels

For the identification of a genus level Salmonella RAPD marker a positive test panel consisting of a variety of Salmonella subgenera was constructed to insure that the marker would include a broad range of Salmonella strains. The positive test panel contained of the following Salmonella serotypes: Subgenus I; *S. typhimurium, S. typhi, S. enteritidis, S. saintpaul, S. binza, S. napoli, S. clerkwell, S. infantis, S. newport, S. heidelberg, S. virchow, S. stanley, S. senftenberg, S. gallinarium, S. cholerasuis, S. paratyphi, S. bredeney, S. kedougou, S. montevideo, S. hadar, S. panama, S. braenderup, S. blockley, S. agona, S. brandenberg, S. anatum, S. thompson, S. berta, S. manchester, S. ealing, S. eastbourne, S. indiana, S. weltevreden, S. bracknell, S. bovismorbificans, S. barelily, S. bristol, S. bergen, S. berkeley, S. birkinhead, S. austin, S. areaget, S. blukwa, S. bonn, S. brazil, S. butantan, S. bodjonegro, S. adelaide, S. allandale, S. albuquerque, S. aequatoria, abaetetube, S. alabama, S. alachua,* and *S. chicago*; Subgenus II; *S. artis, S. bloemfontein, S. bulawayo, S. bleadon, S. betioky, S. basel*; Subgenus IIIa; *S. arizonae*; Subgenus V; *S. brookfield.*

The negative test panel in the screening for a RAPD marker specific to Salmonella consisted of the following species; *Escherichia coli, Escherichia blattae, Escherichia fregusonii, Escherichia hermani, Escherichia vulneris, Shigella sonnei, Shigella flexneri, Shigella dysenteria, Shigella boydii, Citrobacter diversus,* and *Citrobacter freundii.* These species represent a sampling of strains which are not included within the genus Salmonella but are genetically similar to Salmonella. If strains representing these species show a substantially different RAPD pattern when amplified with the arbitrary primer used to generate the Salmonella marker, and if the selected Salmonella marker is absent from the pattern, it is expected that the marker sequence will be selective for Salmonella.

Example 1

ISOLATION OF DIAGNOSTIC FRAGMENT FROM SALMONELLA SP. RAPD Screen Test Results:

Genomic DNA was isolated from members of both the positive and negative test panel members (above) and used to screen eight, 12-base primers of arbitrary sequence. These primers were used to generate RAPD patterns for strains representing the positive and negative test panels. The primers used in the initial RAPD screening are listed in Table I.

TABLE I

Twelve-Base Arbitrary Primers Used in the Generation of RAPD Patterns for the Purpose of Identifying a Specific Genus Level Salmonella Marker

| | | | | | |
|---|---|---|---|---|---|
| 12CN01 | AGC | TGA | TGC | TAC | (Sequence ID No. 2) |
| 12CN02 | AGT | CGA | ACT | GTC | (Sequence ID No. 3) |
| 12CN03 | TTA | GTC | ACG | GCA | (Sequence ID No. 4) |
| 12CN04 | TGC | GAT | ACC | GTA | (Sequence ID No. 5) |
| 12CN05 | CTA | CAG | CTG | ATG | (Sequence ID No. 6) |
| 12CN06 | GTC | AGT | CGA | ACT | (Sequence ID No. 7) |
| 12CN07 | GGC | ATT | AGT | CAC | (Sequence ID No. 8) |
| 12CN08 | CGT | ATG | CGA | TAC | (Sequence ID No. 9) |

The primers were used individually and as mixed pairs in the following amplification protocol;

For each 50 µl reaction, 2 µl—dNTP mix (5 mM dNTP each), 35 µl deionized water, 5 µl—10× reaction buffer (500 mM KCl, 100 mM tris @ pH 8.3, 15 mM MgCl$_2$, 0.003% gelatin), 2.5 µl—each primer (10 mM) (5 µl if only one primer is used), 0.4 µl Taq polymerase (5 U/µl), and 1.2 µl Taq dilution buffer (10 mM tris @ pH 8.0 and 1.0% Tween 20) were combined. 1.0 µl—genomic bacterial DNA @ 50 ng/µl was added. The reaction was heated to 94° C. for 5 minutes. 32 cycles of the following temperature cycle were run; 1' @ 94°, 5' @ 46°, 2' ramp to 72° C., and 2 µl @ 2° C. A 5 µl aliquot of the reaction was combined with 2 µl of Ficol-loading buffer and run on a 4% acrylamide gel (29:1) /1.0× TBE.

FIG. 1A shows the RAPD patterns as separated by gel electrophoresis for samples of 16 different species of Salmonella from the positive test panel which was amplified with a single primer, 12CN03. The lanes are correlated with the Salmonella species as follows:

| Lane | Species and I.D. No. |
|---|---|
| 1 | S. typhimurium 587 (ATCC 29057) |
| 2 | S. typhimurium 588 (ATCC 29631) |
| 3 | S. binza 1085 |
| 4 | S. napoli 966 |
| 5 | S. enteritidis 1109 |
| 6 | S. enteritidis 737 |
| 7 | S. newport 707 (ATCC 6962) |
| 8 | S. arizonae 725 (ATCC 13314) |
| 9 | S. infantis 728 |
| 10 | S. heidelberg 577 |
| 11 | S. virchow 738 |
| 12 | S. stanley 739 |
| 13 | S. senftenberg 740 |
| 14 | S. gallinarium 741 |
| 15 | S. cholerasuis 917 (ATCC 13312) |
| 16 | S. paratyphi A 918 (ATCC 9150) |

Standard amplification conditions for amplification of DNA from the positive test panel consisted of 0.2 mM dNTPs, 1 µM 12CN03 primer and a reaction buffer of 50 mM KCl, 10 mM tris @ pH 8.3, 1.5 mM MgCl$_2$, and 0.0003% gelatin. A total of 32 cycles were run under the following conditions: 1' at 94° C.; 5' at 46° C.; 2' ramp to 72° C. and 2' at 72° C.

The final cycle was followed by an additional 9' at 72° C. Unlabeled lanes contain molecular weight markers of the following sizes; 228, 412, 693, 1331, and 2306 base pairs (bp). RAPD amplification products were electrophoresed in 4% acrylamide/bisacrylamide (29/1) using a 1.0× tris-borate-EDTA running buffer for 55 minutes at a field strength of 14 V/cm. Following electrophoresis the gels were stained for 15 minutes in a solution of ethidium bromide at 0.25 µg/ml.

As is evident by FIG. 1A the positive test panel produced two characteristic amplification products of 800 and 2000 bp, which appeared in over 90% of the 91 Salmonella strains tested.

Figure 1B:
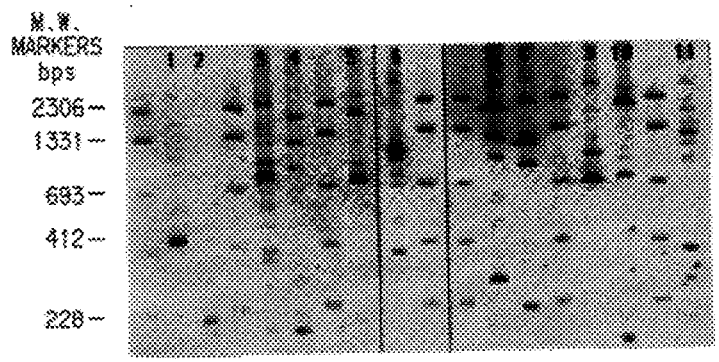
FIG. 1B is a composite photograph showing electrophoretic marker profiles of amplification products for DNA from the negative test panel comprising a variety of non-Salmonella bacterial strains amplified with a single RAPD primer, 12CN03 (Sequence ID No. 4).
Figure 4A:
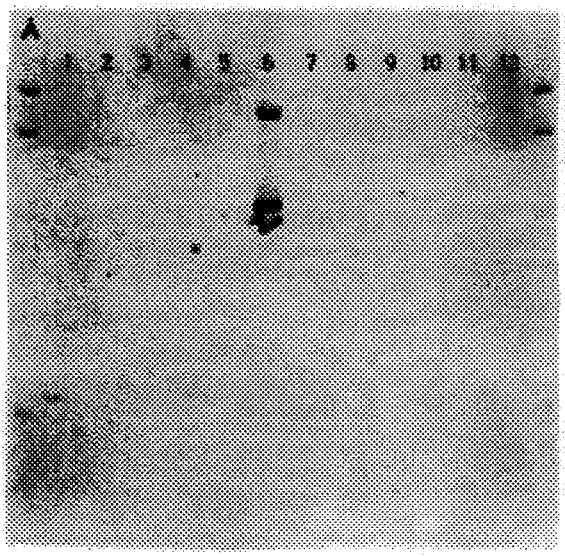
FIG. 4A is a photograph showing PCR amplification products formed using the 60-26 (SEQ ID NO.:15) 761rc-26 (SEQ ID NO.:19) primer set as separated by gel electrophoresis for samples of 11 non-Salmonella strains and one Salmonella positive control in lane 6.
Figure 4B:
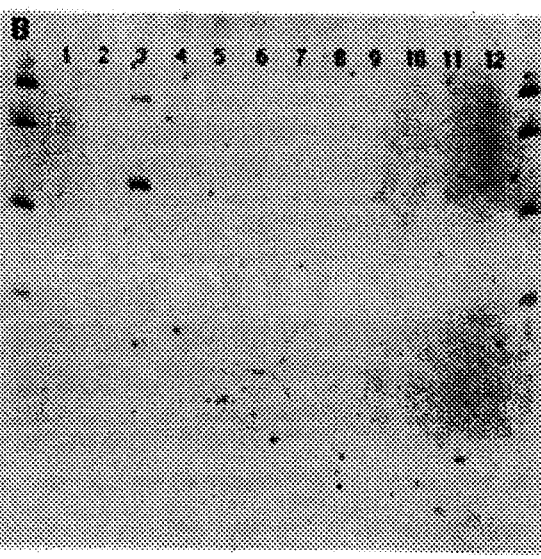
FIG. 4B is a photograph showing PCR amplification products formed using the 60-26 (SEQ ID NO.:19)/ 761rc-26 (SEQ ID NO.:20) primer set as separated by gel electrophoresis for samples of an additional 11 non-Salmonella strains and one Salmonella positive control in lane 3.
Figure 4C:
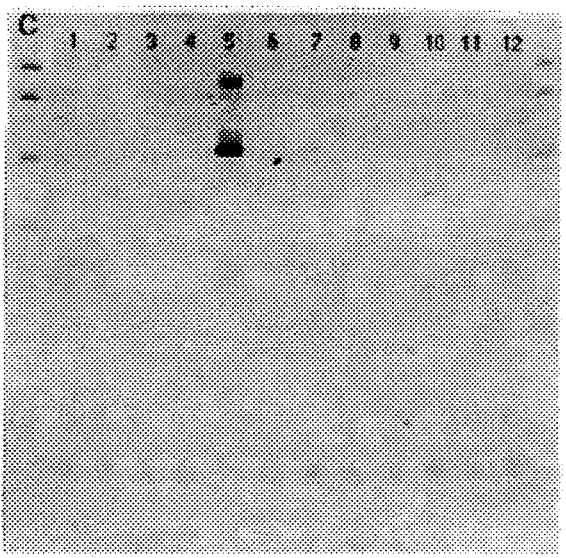
FIG. 4C is a photograph showing PCR amplification products formed using the 60-26 (SEQ ID NO.:19)/ 761rc-26 (SEQ ID No.:20) primer set as separated by gel electrophoresis for samples of an additional 11 non-Salmonella strains and one Salmonella positive control in lane 5.
Figure 4D:
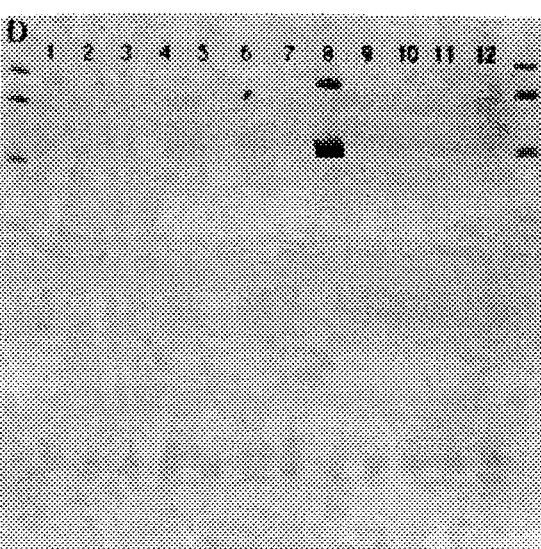
FIG. 4D is a photograph showing PCR amplification products formed using the 60-26 (SEQ ID NO.:19)/ 761rc-26 (SEQ ID NO.:20) primer set as separated by gel electrophoresis for samples of an additional 11 non-Salmonella strains and one Salmonella positive control in lane 8.
Figure 5A:
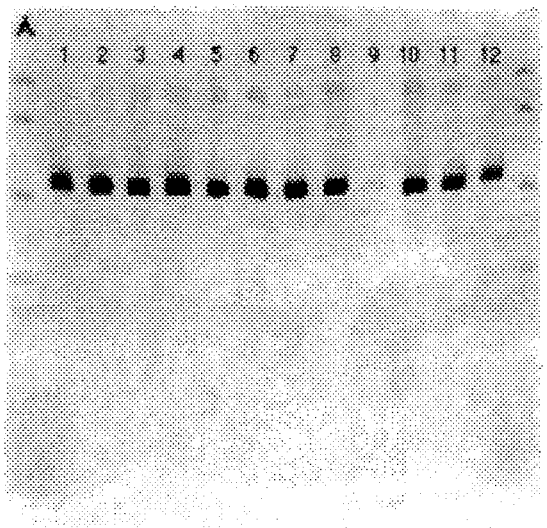
FIG. 5A is a photograph showing PCR amplification products formed using primer #6-26 (SEQ ID NO.:15) and primer #761rc-26 (SEQ ID NO.:19) as separated by gel electrophoresis for samples of 11 Salmonella strains. One blank was used in the set at lane 9.
Figure 5B:
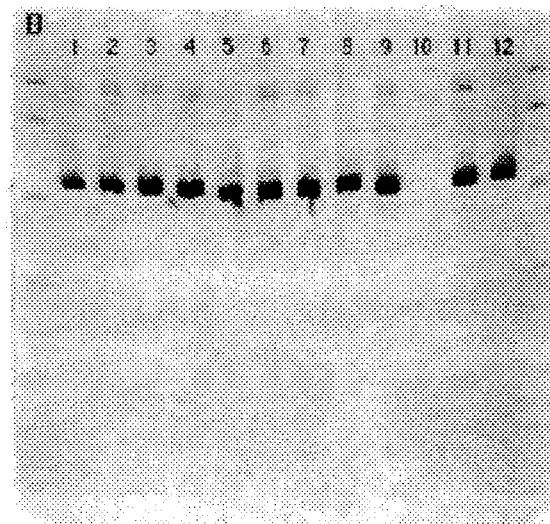
FIG. 5B is a photograph showing PCR amplification products formed using primer #6-26 (SEQ ID NO.:15) and primer #761rc-26 (SEQ ID NO.:19) as separated by gel electrophoresis for samples of a further 11 Salmonella strains. One blank was used in this set at lane 10 as a control.
Figure 5C:
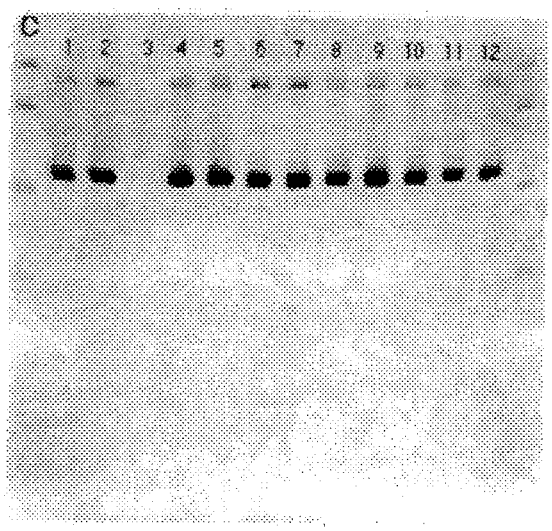
FIG. 5C is a photograph showing PCR amplification products formed using primer #6-26 (SEQ ID NO.:15) and primer #761rc-26 (SEQ ID NO.:19) as separated by gel electrophoresis for samples of a further 11 Salmonella strains. One blank was used in this set at lane 3 as a control.
Figure 5D:
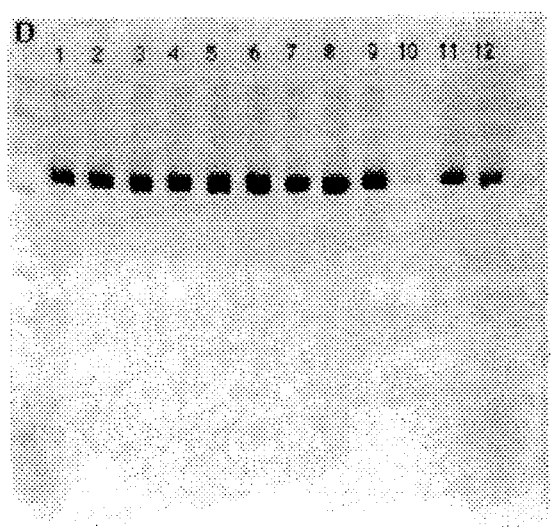
FIG. 5D is a photograph showing PCR amplification products formed using primer #6-26 (SEQ ID NO.:15) and primer #761rc-26 (SEQ ID NO.:19) as separated by gel electrophoresis for samples of a further 11 Salmonella strains. One blank was used in this set at lane 10 as a control.

FIG. 1B shows the RAPD patterns as separated by gel electrophoresis for samples of 13 different species of a variety of Salmonella bacteria from the negative test panel which were amplified with a single primer, 12CN03. The lanes are correlated with the bacterial species as follows:

| Lane | Species and I.D. No. |
|---|---|
| 1 | Shigella sonnei 702 |
| 2 | Shigella flexneri 1083 (ATCC 29903) |
| 3 | Shigella dysenteria 1082 (ATCC 13313) |
| 4 | Shigella boydii 1081 (ATCC 8700) |
| 5 | Citrobacter diversus 97 |
| 6 | Citrobacter freundii 383 (ATCC 8700) |
| 9 | Escherichia coli 90 |
| 10 | Escherichia blattae 846 (ATCC 29907) |
| 11 | Escherichia fregusonii 847 (ATCC 35469) |
| 12 | Escherichia hermani 848 (ATCC 33650) |
| 13 | Escherichia vulneris 850 (ATCC 33821) |

Standard amplification conditions for the amplification of the negative test panel consisted of 0.2 mM dNTPs, 1 µM 12CN03 primer and a reaction buffer of 50 mM KCl, 10 mM tris @ pH 8.3, 1.5 mM MgCl$_2$, and 0.0003% gelatin. A total of 32 cycles were run under the following conditions: 1' at 94° C.; 5' at 46° C.; 2' ramp to 72° C. and 2' at 72° C. The final cycle was followed by an additional 9' at 72° C. Molecular weight markers, gel composition, electrophoresis and staining conditions were as described above for the positive test panel.

As is evident by the data in FIG. 1B, none of the negative test panel group showed the 800 bp or 2000 bp amplification products seen in the positive test panel.

Extraction and Sequencing of the Salmonella diagnostic Fragment:

The 800 bp product for Salmonella typhimurium 587 (ATCC #29057) was selected for extraction and sequencing. The amplification product was isolated by electrophorests in a low melting point agarose. The fragment was cut from the gel and extracted onto GlassMilk™ using a customized procedure from the Geneclean kit sold by Bio 101 Inc. The fragment was then eluded and reamplified with the 12CN03 primer to provide quantities of DNA suitable for sequencing.

Since both ends of the fragment contain the same 12 base sequence, priming the parent diagnostic fragment with the 12CN03 primer would result in the production of two simultaneous sequences superimposed upon each other, which could not be resolved into the individual single-stranded sequences. Hence, it was necessary to carry out a restriction endonuclease digestion of the amplified 12CN03 product prior to running the sequencing reaction. Digest products were separated electrophoretically in low melting agarose and the appropriate restriction product was reisolated using the Geneclean procedure. The individual purified restriction digest products were then sequenced using 12CN03 as a sequencing primer. The restriction fragments were sequenced by the Sanger chain-termination method using fluorescence-labeled dideoxynucleotides and the Genesis 2000™ DNA Analysis System.

An example of the sequencing protocol used is as follows:

Combine 1.5 µl—purified digest product (est. 100 ng), 3.5 µl—12CN03 @ 10.0 ng/µl and 28.5 µl—$H_2O$ and heat to 95° C. for 2 minutes. Immediately place the mixture on wet ice. Add the following mixture 10 µl—5× reverse transcriptase reaction buffer (300 mM tris @ pH 8.3, 375 mM NaCl, 37.5 mM $MgCl_2$), 6.5 µl—dNTP stock (180 uM ea.), 0.65 µl—ddNTP stock (250 µM 505 nm-ddGTP, 800 µM 512 nm-ddATP, 210 µM 519 nm-ddCTP and 700 µM 526 nm-ddTTP) and 1 µl—reverse transcriptase. Vortex, centrifuge and then incubate at 46° C. for 15 minutes. Separate the sequencing products on a spin column and vacuum dry. Wash with 150 µl of cold 70% ethanol and centrifuge 5 min. Vacuum dry and reconstitute in 3 µl formamide.

The labeled sequencing products were then analyzed by the Genesis 2000™ DNA Analysis System. Once differential sequence had been determined at both ends of the Salmonella target fragment the remaining sequence information was obtained through the use of either asymmetric PCR to generate single-stranded DNA or a modified double-stranded DNA sequencing protocol using double-stranded PCR product. The modification in the double-stranded protocol consisted of using a 46° C. annealing temperature and a primer:template ratio of 25:1. This ratio is significantly higher than is generally practiced in sequencing reactions. At such a large primer:template ratio, priming at multiple sites is generally observed with single-stranded templates. However, when the template consists of short linear double-stranded DNA, successful priming can only occur at 5' blunt ends of the template and only with a primer whose sequence matches that end. The net result is that only a single discrete sequencing product is observed under these conditions. The sequence of the complete Salmonella fragment is shown in FIG. 2.

Example 2

DETERMINATION OF POLYMORPHIC POSITIVE TEST PANEL STRAINS

The following procedure was used to determine which strains of Salmonella were most "polymorphic" with respect to the sequence of the diagnostic fragment shown in FIG. 2. Two sets of amplification primer pairs were arbitrarily selected from the marker sequence. The sequence of these primers is shown in Table II.

Primer nomenclature:

The first number indicates the 3' position of the primer on the Salmonella target sequence in FIG. 2. The rc indicates that the primer sequence is derived from the reverse complementary strand. The 23 indicates the length of the primer.

Amplifications were carried out on DNA isolated from 740 strains of Salmonella representing all six subgenus groups for each of the primer sets, 54-23/665rc-23 and 126-23/648rc/23. Standard amplification conditions consisted of 0.2 mM dNTPs, 0.5 µM each primer and a reaction buffer of 50 mMKCl, 10 mM tris @ pH 8.3, 1.5 mM $MgCl_2$, and 0.0003% gelatin. A total of 35 cycles were run under the following conditions: 15 seconds at 94° C.; 2 minutes at 69° C. and 1 minute at 72° C. The final cycle was followed by an additional 7 minutes at 72° C. Gel composition, electrophoresis and staining conditions were as described above for the positive test panel in Example 1.

Strains of Salmonella were classified as a "polymorphic" if they produced amplification products that fell into the following categories:

i) weak, inconsistent, or total lack of production of an amplification product;

ii) amplification products which are larger or smaller than the generally observed amplification product;

iii) the presence of more than one amplification product.

Examples of these types of polymorphic amplification events are shown in FIG. 3. FIG. 3 shows the amplification product patterns as separated by gel electrophoresis for samples of 6 polymorphic and 6 normal Salmonella amplified with the primers of Table II. The lanes are correlated with the Salmonella strains as follows:

| Lane | Species and I.D. No. |
|---|---|
| 1 | S. arizonae 1573 |
| 2 | S. arizonae 1572 |
| 3 | S. typhimurium 708 (ATCC 13311) |
| 4 | S. arizonae 726 (ATCC 12324) |
| 5 | S. oranienburg 2212 |
| 6 | S. Subgenus Group I 2213 |
| 7 | S. Subgenus Group II 1514 |
| 8 | S. Subgenus Group V 1535 |
| 9 | S. Subgenus Group IV 1714 |
| 10 | S. Subgenus Group V 1773 |
| 11 | S. Subgenus Group I 1513 |
| 12 | S. Subgenus Group I 1517 |

From the original group of 740 Salmonella strains a group of 43 polymorphic Salmonella were selected.

Example 3

EVALUATION OF PRIMING SITES WITHIN THE DIAGNOSTIC FRAGMENT FOR THE BEST GENUS LEVEL INCLUSIVITY OF SALMONELLA

Example 3 illustrates the method used to identify which priming sites within the diagnostic Salmonella fragment showed the best inclusivity for Salmonella at the genus level.

TABLE II

Primers used in the determination of polymorphic Salmonella

| #54-23 | GAC | GCT | TAA | TGC | GGT | TAA | CGC | CA | (Sequence ID No. 10) |
| #126-23 | AAC | CAT | GCA | TCA | TCG | GCA | GAA | CG | (Sequence ID No. 11) |
| #648rc-23 | AGT | AGC | CTG | CCG | CTT | ACG | CTG | AA | (Sequence ID No. 12) |
| #665rc-23 | TCA | GGA | TGC | AGG | CGA | TAG | TAG | CC | (Sequence ID No. 13) |

Primers were prepared for a large number sites at both ends of the Salmonella target sequence. Amplifications were carried out on genomic DNA from the 43 polymorphic Salmonella for a variety of these primer combinations according to the protocol listed below. In cases where a given primer combination produced an amplification product in over 90% of the polymorphic Salmonella, additional primers were then prepared which moved one of the priming sites upstream or downstream one base at a time. Once the priming site that found the highest portion of polymorphic Salmonella was identified, that site was fixed and then additional primers were prepared which moved the priming site at the other end of the Salmonella target sequence loading buffer and run on a 4% acrylamide gel (29:1)/1.0× TBE. Sample responses were graded as follows:

If a PCR product was visible at $<5 \times 10^4$ DNA copies per reaction the result was scored as +1.

If a PCR product was only visible when the DNA copy number was $>5 \times 10^4$ copies per reaction the test was scored as +0.5.

The scores for the 43 strains were summed and divided by 43. The results of the evaluation were assembled in Table III.

TABLE III

| 3'/3' | 534 | 536 | 648 | 649 | 663 | 664 | 665 | 666 | 667 | 755 | 757 | 759 | 760 | 761 | 762 | 763 | 766 | 770 | 774 |
|---|---|---|---|---|---|---|---|---|---|---|---|---|---|---|---|---|---|---|---|
| 38 | | | | | | | | | | | | | | | | | 0.72 | | |
| 58 | | | | | | | 0.9 | | | | | | | | | | | | |
| 59 | 0.975 | 0.99 | | | | | 0.94 | | | | | | | 0.9 | | | | | |
| 60 | 0.965 | 0.94 | 0.73 | | 0.82 | 0.7 | 0.95 | 0.85 | 0.9 | 0.9 | 0.9 | 0.83 | 0.9 | 0.965 | 0.9 | 0.92 | 0.9 | 0.8 | 0.76 |
| 61 | | | | | | | | | | | | | | 0.71 | | | | | |
| 62 | | | | | | | | | | | | | | 0.65 | | | | | |
| 64 | | | | | | | 0.91 | | | | | | | | | | | | |
| 65 | | | | | | | | | | | | | | 0.82 | | | | | |
| 72 | | | | | | | | | | | | | | 0.78 | | | | | |
| 125 | | | | | | | | | | | | | | 0.82 | | | | | |
| 126 | | | | 0.71 | | | | | | | | | | | | | | | |
| 127 | | | 0.61 | | | | 0.68 | | | | | | | | | | | | |
| 135 | | | | | | | 0.5 | | | | | | | | | | | | | upstream or downstream one base at a time. The combination of priming sites which produced an amplification product for the highest percentage of polymorphic Salmonella would then be evaluated at the next stage of the screening procedure.

Primer-screening amplification reactions were conducted using the following procedure: Combine 1.5 µl—dNTP mix (5 mM each dNTP), 40 µl—deionized water, 5 µl—10× reaction buffer (500 mM KCl, 100 mM tris @ pH 8.3, 15 mM $MgCl_2$, 0.003% gelatin) 0.4 µl—Taq polymerase (5U/µL), 1.2 µl—Taq dilution buffer (10 mM tris @ pH 8.0 and 1.0% Tween 20), 0.66 µl—each primer (26-mer @ 10 µM), and 1.0 µl—genomic DNA @ 50 ng/µl. Heat to 94° C. for 2 minutes. Run 35 cycles of 15"@ 94° C.; 3' @ 72° C. Combine a 5 µl aliquot of the reaction with 2 µl of Ficol- The numbers on the rows and columns represent the 3' positions relative to Sequence ID No. 1 of the two primers used in the amplification reaction. Based on the results of the primer site evaluation, four locations on the target sequence were sufficiently well conserved to yield priming sites capable of capturing over 95% of the polymorphic Salmonella. These sites were found in the following locations on the target sequence as displayed in FIG. 2; 59–60, 534–536, 665 and 761. The 761 and 534 sites were selected over the 665 site because priming sites surrounding the 761 and 534 base positions detected a higher portion of the polymorphic Salmonella. Both the 59 and 60 sites were evaluated as possible priming sites for the complementary strand of the target. The sequences for these primers are shown in Table IV.

TABLE IV

| Primer Sequences Found in at Least 95% of the Polymorphic Salmonella | | | | | | | | | | |
|---|---|---|---|---|---|---|---|---|---|---|
| #59-26 | TTA | GCC | GGG | ACG | CTT | AAT | GCG | GTT | AA | Sequence ID No. 14 |
| #60-26 | TAG | CCG | GGA | CGC | TTA | ATG | CGG | TTA | AC | Sequence ID No. 15 |
| #534rc-26 | CTA | TTT | TCT | GGC | CTG | ACG | CTA | TGA | CC | Sequence ID No. 16 |
| #536rc-26 | TTC | TAT | TTT | CTG | GCC | TGA | CGC | TAT | GA | Sequence ID No. 17 |
| #665rc-26 | CAT | TCA | GGA | TGC | AGG | CGA | TAG | TAG | CC | Sequence ID No. 18 |
| #761rc-26 | CTT | TAC | CGC | TTC | CAG | TGT | GGC | CTG | AA | Sequence ID No. 19 |

Primer nomenclature:

The first number indicates the 3' position of the primer on the Salmonella target sequence in FIG. 2. The rc indicates that the primer sequence is derived from the reverse complementary strand. The 26 indicates the length of the primer.

Example 4

EVALUATION OF LARGER POPULATIONS OF NEGATIVE AND POSITIVE TEST PANELS

Since the presence of bacteria in the genus Salmonella will be determined based on the production of an amplification product generated from the primers now being screened, it is necessary to conduct a broader sampling of strains representing the negative and positive test panels.

The selectivity of the Salmonella primer sets was evaluated by testing representatives of the following species representing the negative test panel to determine whether they contained DNA sequences which were amplifiable with either the 60-26/761rc-26 primer set or any combination of primers 59-26 or 60-26 with 534rc-26 or 536rc-26; *Escherichia coli, Shigella sonnei, Shigella dysenteria, Shigella flexneri, Shigella boydii, Enterobacter cloacae, Enterobacter agglomeran, Enterobacter aerogenes, Citrobacter freundii, Citrobacter diversus, Hafnia alvei, Proteus mirabilis, Proteus morganii, Proteus vulgaris, Klebsiella pneumoniae, Serratia marcescens, Yersinia enterocolitica, Listeria monocytogenes, Listeria innocua, Listeria ivanovii, Staphylococcus aureus, Staphylococcus warneri, Staphylococcus saprophyticus, Staphylococcus epidermidis, Enterococcus faecalis, Bacillus cereus, Bacillus thuringiensis, Bacillus subtilis.*

A representative composite showing PCR amplification products for the non-Salmonella strains listed below is shown in FIG. 4. FIG. 4 shows the amplification products formed using the 60-26/761rc-26 primer set as separated by gel electrophoresis for samples of 44 non-Salmonella. Four strains of Salmonella were also included in the reaction set as a positive control to indicate that conditions were sufficient for amplification of the Salmonella target sequence to take place. The lanes are correlated with the non-Salmonella and Salmonella strains as follows:

| Lane | Species and I.D. No. |
|---|---|
| | A |
| 1 | *Escherichia coli* 25 |
| 2 | *Escherichia coli* 33 |
| 3 | *Escherichia coli* 57 |
| 4 | *Escherichia coli* 84 |
| 5 | *Escherichia coli* 139 |
| 6 | *Salmonella typhimurium* 897 |
| 7 | *Enterobacter cloacae* 123 |
| 8 | *Enterobacter cloacae* 221 |
| 9 | *Enterobacter cloacae* 313 |
| 10 | *Enterobacter cloacae* 375 (ATCC 13047) |
| 11 | *Proteus mirabilis* 360 |
| 12 | *Proteus mirabilis* 364 |
| | B |
| 1 | *Proteus morganii* 99 |
| 2 | *Proteus morganii* 363 |
| 3 | *Salmonella enteritidis* 1109 |
| 4 | *Proteus vulgaris* 273 |
| 5 | *Proteus vulgaris* 275 |
| 6 | *Proteus vulgaris* 385 (ATCC 13315) |
| 7 | *Proteus vulgaris* 959 |
| 8 | *Enterobacter agglomerans* 905 |
| 9 | *Enterobacter aerogenes* 62 |
| 10 | *Enterobacter aerogenes* 376 |

-continued

| Lane | Species and I.D. No. |
|---|---|
| | (ATCC 13048) |
| 11 | *Klebsiella pneumoniae* 373 (ATCC 13883) |
| 12 | *Klebsiella pneumoniae* 749 |
| | C |
| 1 | *Listeria monocytogenes* 938 |
| 2 | *Listeria monocytogenes* 941 |
| 3 | *Listeria innocua* 1157 |
| 4 | *Listeria ivanovii* 1167 |
| 5 | *Salmonella infantis* 908 |
| 6 | *Citrobacter freundii* 361 |
| 7 | *Citrobacter freundii* 896 |
| 8 | *Citrobacter diversus* 217 |
| 9 | *Hafnia alvei* 934 |
| 10 | *Serratia marcesens* 372 |
| 11 | *Enterococcus faecalis* 283 (ATCC 19433) |
| 12 | *Yersinia enterocolitica* 750 |
| | D |
| 1 | *Staphylococcus aureus* 118 |
| 2 | *Staphylococcus aureus* 207 |
| 3 | *Staphylococcus aureus* 610 |
| 4 | *Staphylococcus aureus* 812 |
| 5 | *Staphylococcus warneri* 793 |
| 6 | *Staphylococcus saprophyticus* 762 |
| 7 | *Staphylococcus saprophyticus* 788 |
| 8 | *Salmonella saintpaul* 1086 |
| 9 | *Shigella sonnei* 701 |
| 10 | *Shigella boydii* 1081 (ATCC 8700) |
| 11 | *Shigella dysenteria* 1082 (ATCC 13313) |
| 12 | *Shigella flexneri* 1083 (ATCC 29903) |

Of the 100 strains which were evaluated only one strain which was tentatively identified as *Hafnia alvei*, gave a false positive result with the 60-26 and 761rc-26 primer set. The identity of this false positive is considered ambiguous because although its ribotyping pattern appears to be closer to *Hafnia alvei* than to the genus Salmonella, the strain appears to be biochemically closer to Salmonella. The remaining 35 strains of *Hafnia alvei*, which were screened all tested negative for the presence of the Salmonella test sequence. Primer combinations using 3' sites at base positions 59 or 60 along with complementary strand priming sites at 534.or 536 all generated amplification products with at least 20% of the negative test panel. Since this rate of false positives was unacceptable for use in the preferred embodiments only the 60-26 and 761rc-26 primer set was selected for the further evaluation. The fragment of FIG. 2 flanked and included by these primers included nucleic acid bases starting at position 35 and ending at position 786; this is the diagnostic target of the invention for Salmonella. Position 35 to 786 of Sequence ID No. 1 is designated Sequence ID No. 21. Position 35 to 786 of Sequence ID No. 20 is designated as Sequence ID No. 22.

The detection efficiency of the diagnostic marker primers 60-26 and 761rc-26 primers was then evaluated on a test group of over 1480 Salmonella strains. A breakdown of the test group by subgenus group and serotype is shown in Table V.

TABLE V

List of Salmonella Serotypes Comprising the Test Group for the 60-26 and 761rc-26 Primers

| Serotype/Subgenus | No. | Serotype/Subgenus | No. |
|---|---|---|---|
| Salmonella abaetetuba F | 3 | Salmonella london E1 | 2 |
| Salmonella adabraka E1 | 1 | Salmonella madelia H | 2 |
| Salmonella adelaide O | 11 | Salmonella manchester C2 | 3 |
| Salmonella agama B | 2 | Salmonella manhatten C2 | 5 |
| Salmonella agona O | 25 | Salmonella manila E2 | 2 |
| Salmonella ajiobo G2 | 2 | Salmonella mbandaka C1 | 14 |
| Salmonella alabama D1 | 2 | Salmonella meleagridis E1 | 3 |
| Salmonella albany C3 | 5 | Salmonella minnesota L | 5 |
| Salmonella altendorf B | 2 | Salmonella mississippi G2 | 4 |
| Salmonella amsterdam E1 | 7 | Salmonella montevideo C1 | 9 |
| Salmonella anatum E1 | 42 | Salmonella morehead N | 2 |
| Salmonella arechavaleta B | 2 | Salmonella muenchen C2 | 11 |
| Salmonella arkansas E3 | 11 | Salmonella muenster E1 | 10 |
| Salmonella austin C1 | 2 | Salmonella napoli D1 | 7 |
| Salmonella bareilly C1 | 8 | Salmonella newbrunswick E2 | 5 |
| Salmonella berta D1 | 13 | Salmonella newington E2 | 1 |
| Salmonella binza E2 | 19 | Salmonella newport C2 | 26 |
| Salmonella blockley C2 | 4 | Salmonella nyborg E1 | 2 |
| Salmonella bodjonegoro N | 2 | Salmonella ohio C1 | 53 |
| Salmonella braenderup C1 | 30 | Salmonella oranienburg C1 | 8 |
| Salmonella brandenburg B | 9 | Salmonella othmarschen C1 | 5 |
| Salmonella bredeney B | 14 | Salmonella panama D1 | 8 |
| Salmonella california B | 7 | Salmonella paratyphi A | 1 |
| Salmonella cerro K | 13 | Salmonella poona G1 | 2 |
| Salmonella champaign Q | 2 | Salmonella pullorum D1 | 21 |
| Salmonella chandans F | 5 | Salmonella reading B | 8 |
| Salmonella choleraesuis C1 | 13 | Salmonella redlands I | 2 |
| Salmonella corvallia C3 | 6 | Salmonella rostock D1 | 2 |
| Salmonella cubana G2 | 21 | Salmonella rubislaw F | 5 |
| Salmonella daressalaam B | 1 | Salmonella saintpaul B | 10 |
| Salmonella derby B | 8 | Salmonella sandiego B | 7 |
| Salmonella drypool E2 | 11 | Salmonella santiago C3 | 48 |
| Salmonella dublin D1 | 14 | Salmonella schwarzengr. B | 10 |
| Salmonella durham G2 | 5 | Salmonella sculcoates | 2 |
| Salmonella ealing O | 3 | Salmonella senftenberg E4 | 56 |
| Salmonella enteritidis D1 | 124 | Salmonella sladun B | 2 |
| Salmonella eschweiler C1 | 2 | Salmonella stanley B | 7 |
| Salmonella ferlac H | 2 | Salmonella stanleyville B | 3 |
| Salmonella gallinarum O | 3 | Salmonella sya X | 4 |
| Salmonella give E1 | 4 | Salmonella tennessee C1 | 19 |
| Salmonella haardt O | 12 | Salmonella thomasville E3 | 11 |
| Salmonella hadar C2 | 17 | Salmonella thompson C1 | 16 |
| Salmonella havana G2 | 15 | Salmonella typhi D1 | 2 |
| Salmonella heidelberg B | 20 | Salmonella typhimurium B | 97 |
| Salmonella indiana B | 13 | Salmonella urbana N | 2 |
| Salmonella infantis C1 | 31 | Salmonella virchow C1 | 14 |
| Salmonella johannesburg R | 5 | Salmonella waycross S | 2 |
| Salmonella kedougou G2 | 7 | Salmonella worthington G2 | 11 |
| Salmonella kentucky C3 | 11 | Salmonella Group I species | 211 |
| Salmonella kiambu B | 2 | Salmonella Group II species | 23 |
| Salmonella krefeld E4 | 2 | Salmonella Group IIIa species | 39 |
| Salmonella kubacha B | 4 | Salmonella Group IIIb species | 19 |
| Salmonella lexington E1 | 7 | Salmonella Group IV species | 16 |
| Salmonella lille C1 | 8 | Salmonella Group V species | 2 |
| Salmonella livingston C1 | 9 | | |

This pair of priming sites proved to be extremely accurate in detecting Salmonella strains from all six subgenus groups in the genus Salmonella. The 1390 strains of Group I Salmonella were detected at an efficiency of 99.75%. Although the remaining five subgenus groups contained considerably fewer strains, the strains comprising all these groups were detected at 100% efficiency. The detection efficiency of the 60 and 761 priming sites for the individual subgenus groups and the entire Salmonella test group are shown in Table VI.

TABLE VI

Summary of Salmonella Detecting Efficiency for the 60-26 and 761rc-26 Primer Set

| | |
|---|---|
| Total Subgenus Group I Tested | 1390 |
| Total Positive | 1386.5 |
| % Positive | 99.75 |
| Total Subgenus Group II Tested | 23 |
| Total Positive | 23 |
| % Positive | 100 |
| Total Subgenus Group IIIa Tested | 39 |
| Total Positive | 39 |
| % Positive | 100 |
| Total Subgenus Group IIIb Tested | 19 |
| Total Positive | 19 |
| % Positive | 100 |
| Total Subgenus Group IV Tested | 16 |
| Total Positive | 16 |
| % Positive | 100 |
| Total Subgenus Group V Tested | 2 |
| Total Positive | 2 |
| % Positive | 100 |
| Total Salmonella Tested | 1489 |
| Total Salmonella Positive | 1485.5 |
| % Positive | 99.76 |

If a PCR product was visible at $<5 \times 10^4$ DNA copies per reaction the result was scored as +1.

If a PCR product was only visible when the DNA copy number was $>5 \times 10^4$ copies per reaction the test was scored as +0.5.

A representative composite showing PCR amplification products for the Salmonella strains listed below is shown in FIG. 5.

FIG. 5 shows the amplification products formed using the 60-26/761rc-26 primer set as separated by gel electrophoresis for samples of 44 Salmonella. The lanes are correlated with Salmonella strains as follows:

| Lane | Species and I.D. No. |
|---|---|
| | A |
| 1 | Salmonella abaetetuba 1550 |
| 2 | Salmonella adabraka 2340 |
| 3 | Salmonella agona 1353 |
| 4 | Salmonella agona 1446 |
| 5 | Salmonella agona 2339 |
| 6 | Salmonella altendorf 1654 |
| 7 | Salmonella anatum 1501 |
| 8 | Salmonella anatum 2744 |
| 9 | Blank |
| 10 | Salmonella binza 1432 |
| 11 | Salmonella binza 2682 |
| 12 | Salmonella brandenburg 1355 |
| | B |
| 1 | Salmonella enteritidis 706 (ATCC 6962) |
| 2 | Salmonella enteritidis 890 |
| 3 | Salmonella eschweiler 1647 |
| 4 | Salmonella gallinarum 1635 |
| 5 | Salmonella gallinarum 2350 |
| 6 | Salmonella haardt 1344 |
| 7 | Salmonella hadar 1231 |
| 8 | Salmonella havana 2245 |
| 9 | Salmonella havana 2271 |
| 10 | Blank |
| 11 | Salmonella heidelberg 1238 |
| 12 | Salmonella heidelberg 1239 |

| Lane | Species and I.D. No. |
|---|---|
| | C |
| 1 | *Salmonella indiana* 1480 |
| 2 | *Salmonella infantis* 727 |
| 3 | Blank |
| 4 | *Salmonella infantis* 1437 |
| 5 | *Salmonella kedougou* 1251 |
| 6 | *Salmonella kedougou* 1254 |
| 7 | *Salmonella kentucky* 2195 |
| 8 | *Salmonella kentucky* 2756 |
| 9 | *Salmonella kentucky* 2759 |
| 10 | *Salmonella kentucky* 2769 |
| 11 | *Salmonella kiambu* 919 |
| 12 | *Salmonella lexington* 1649 |

| Lane | Species and I.D. No. |
|---|---|
| | D |
| 1 | *Salmonella typhimurium* 1253 |
| 2 | *Salmonella typhimurium* 1499 |
| 3 | *Salmonella typhimurium* 1509 |
| 4 | *Salmonella urbana* 1663 |
| 5 | *Salmonella virchow* 738 |
| 6 | *Salmonella virchow* 1241 |
| 7 | *Salmonella virchow* 1256 |
| 8 | *Salmonella virchow* 1370 |
| 9 | *Salmonella virchow* 1431 |
| 10 | Blank |
| 11 | *Salmonella worthington* 2638 |
| 12 | *Salmonella vrindaban* 2314 |

What is claimed is:

1. An isolated acid fragment having Sequence ID No. 1 or a diagnostic marker thereof or SEQ ID No:20 or a diagnostic marker thereof.

2. An isolated nucleic acid fragment selected from the group of isolated nucleic acid fragments consisting of SEQ ID NO.:4, SEQ ID NO.:14, SEQ ID NO.:15, SEQ ID NO.:16, SEQ ID NO.:17, SEQ ID NO.:18, SEQ ID NO.:19, SEQ ID NO.:21, and SEQ ID NO.:22.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 811 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

```
TTAGTCACGG CAGCCGCGAG GATGATATGG ATGTTAGCCG GGACGCTTAA TGCGGTTAAC      60
GCCATGCCGA CACCAGCGCC CGCCAGCGTG CCGAAACTGT AGAAACCATG CATCATCGGC     120
AGAACGGTTT TATTCAGCTC GCGTTCGACC GCCGCGCCTT CGACATTAAT CGCCACTTCG     180
GCGGCGCCAA AACTGGCGCC GAAAACGGCT AATCCAAGGG CAAAAATCAG CGGCGAGGCG     240
CACCACAGCG CGACGCTAAG AATAACCATC CCGGTTACTG CACAGGTCAT CGTCGTGCGA     300
ATAACCTTCC GGGTGCCAAA TCGTTTCACC AGCCAGGCGG AACAAGAAT ACCGCTCATT      360
GAACCGATAG AAAGCCCGAA TAAGACCGCC CCCATTTCCG CGGTAGAGAC GGAAAGAATA     420
TCCCGAATAG CAGGCGTTCG GGTTGCCCAG GAGGCCATCA GCAGTCCGGG TAAAAGAAG      480
AACATAAACA GCGCCCAGGT ACGGCGTTTT AAGGCGTTAC GTGAGGAGAG GACGGTCATA     540
GCGTCAGGCC AGAAAATAGA AGCGAGAGGT AAACATTAGC AAGCTTGTGT ACATTTGTAC     600
ATATCATCGT CATACTTCAT TGTGCAGACA GTTTTACTG TCTGTTTTTT CAGCGTAAGC      660
GGCAGGCTAC TATCGCCTGC ATCCTGAATG AGATGTGGAA CTCATCATGA AGAAAATGC      720
CGTAAGCGCG CCAATGATCC TAAGCGACGG GAAAAAATAA TTCAGGCCAC ACTGGAAGCG     780
GTAAAGACCT ATGGCACTCT GCCGTGACTA A                                    811
```

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGCTGATGCT AC            12

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGTCGAACTG TC            12

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TTAGTCACGG CA            12

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TGCGATACCG TA            12

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CTACAGCTGA TG            12

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

-continued ( x i ) SEQUENCE DESCRIPTION: SEQ ID NO:7:

GTCAGTCGAA CT                                                                12

( 2 ) INFORMATION FOR SEQ ID NO:8:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:8:

GGCATTAGTC AC                                                                12

( 2 ) INFORMATION FOR SEQ ID NO:9:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:9:

CGTATGCGAT AC                                                                12

( 2 ) INFORMATION FOR SEQ ID NO:10:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:10:

GACGCTTAAT GCGGTTAACG CCA                                                    23

( 2 ) INFORMATION FOR SEQ ID NO:11:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:11:

AACCATGCAT CATCGGCAGA ACG                                                    23

( 2 ) INFORMATION FOR SEQ ID NO:12:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:12:

AGTAGCCTGC CGCTTACGCT GAA                                                    23

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TCAGGATGCA GGCGATAGTA GCC      23

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TTAGCCGGGA CGCTTAATGC GGTTAA      26

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TAGCCGGGAC GCTTAATGCG GTTAAC      26

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CTATTTCTG GCCTGACGCT ATGACC      26

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TTCTATTTTC TGGCCTGACG CTATGA      26

( 2 ) INFORMATION FOR SEQ ID NO:18:

( i ) SEQUENCE CHARACTERISTICS:
        ( A ) LENGTH: 26 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

```
CATTCAGGAT GCAGGCGATA GTAGCC                                              26
```

( 2 ) INFORMATION FOR SEQ ID NO:19:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

```
CTTTACCGCT TCCAGTGTGG CCTGAA                                              26
```

( 2 ) INFORMATION FOR SEQ ID NO:20:

( i ) SEQUENCE CHARACTERISTICS:
( A ) LENGTH: 811 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

```
TTAGTCACGG CAGAGTGCCA TAGGTCTTTA CCGCTTCCAG TGTGGCCTGA ATTATTTTT         60
CCCGTCGCTT AGGATCATTG GCGCGCTTAC GGCATTTTCT TCATGATGA GTTCCACATC        120
TCATTCAGGA TGCAGGCGAT AGTAGCCTGC CGCTTACGCT GAAAAAACAG ACAGTAAAAA        180
CTGTCTGCAC AATGAAGTAT GACGATGATA TGTACAAATG TACACAAGCT TGCTAATGTT        240
TACCTCTCGC TTCTATTTTC TGGCCTGACG CTATGACCGT CCTCTCCTCA CGTAACGCCT        300
TAAAACGCCG TACCTGGGCG CTGTTTATGT TCTTCTTTTT ACCCGGACTG CTGATGGCCT        360
CCTGGGCAAC CCGAACGCCT GCTATTCGGG ATATTCTTTC CGTCTCTACC GCGGAAATGG        420
GGGCGGTCTT ATTCGGGCTT TCTATCGGTT CAATGAGCGG TATTCTTTGT TCCGCCTGGC        480
TGGTGAAACG ATTTGGCACC CGGAAGGTTA TTCGCACGAC GATGACCTGT GCAGTAACCG        540
GGATGGTTAT TCTTAGCGTC GCGCTGTGGT GCGCCTCGCC GCTGATTTTT GCCCTTGGAT        600
TAGCCGTTTT CGGCGCCAGT TTTGGCGCCG CCGAAGTGGC GATTAATGTC GAAGGCGCGG        660
CGGTCGAACG CGAGCTGAAT AAAACCGTTC TGCCGATGAT GCATGGTTTC TACAGTTTCG        720
GCACGCTGGC GGGCGCTGGT GTCGGCATGG CGTTAACCGC ATTAAGCGTC CCGGCTAACA        780
TCCATATCAT CCTCGCGGCT GCCGTGACTA A                                       811
```

( 2 ) INFORMATION FOR SEQ ID NO:21:

( i ) SEQUENCE CHARACTERISTICS:
( A ) LENGTH: 752 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

```
TAGCCGGGAC GCTTAATGCG GTTAACGCCA TGCCGACACC AGCGCCCGCC AGCGTGCCGA         60
```

| | | | | | | |
|---|---|---|---|---|---|---|
|AACTGTAGAA|ACCATGCATC|ATCGGCAGAA|CGGTTTTATT|CAGCTCGCGT|TCGACCGCCG|120|
|CGCCTTCGAC|ATTAATCGCC|ACTTCGGCGG|CGCCAAAACT|GGCGCCGAAA|ACGGCTAATC|180|
|CAAGGGCAAA|AATCAGCGGC|GAGGCGCACC|ACAGCGCGAC|GCTAAGAATA|ACCATCCCGG|240|
|TTACTGCACA|GGTCATCGTC|GTGCGAATAA|CCTTCCGGGT|GCCAAATCGT|TTCACCAGCC|300|
|AGGCGGAACA|AAGAATACCG|CTCATTGAAC|CGATAGAAAG|CCCGAATAAG|ACCGCCCCA|360|
|TTTCCGCGGT|AGAGACGGAA|AGAATATCCC|GAATAGCAGG|CGTTCGGGTT|GCCCAGGAGG|420|
|CCATCAGCAG|TCCGGGTAAA|AAGAAGAACA|TAAACAGCGC|CCAGGTACGG|CGTTTAAGG|480|
|CGTTACGTGA|GGAGAGGACG|GTCATAGCGT|CAGGCCAGAA|AATAGAAGCG|AGAGGTAAAC|540|
|ATTAGCAAGC|TTGTGTACAT|TTGTACATAT|CATCGTCATA|CTTCATTGTG|CAGACAGTTT|600|
|TTACTGTCTG|TTTTTCAGC|GTAAGCGGCA|GGCTACTATC|GCCTGCATCC|TGAATGAGAT|660|
|GTGGAACTCA|TCATGAAAGA|AAATGCCGTA|AGCGCGCCAA|TGATCCTAAG|CGACGGGAAA|720|
|AAATAATTCA|GGCCACACTG|GAAGCGGTAA|AG| | |752|

(2) INFORMATION FOR SEQ ID NO:22:

(i) SEQUENCE CHARACTERISTICS:
        (A) LENGTH: 752 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

| | | | | | | |
|---|---|---|---|---|---|---|
|CTTTACCGCT|TCCAGTGTGG|CCTGAATTAT|TTTTTCCCGT|CGCTTAGGAT|CATTGGCGCG|60|
|CTTACGGCAT|TTTCTTTCAT|GATGAGTTCC|ACATCTCATT|CAGGATGCAG|GCGATAGTAG|120|
|CCTGCCGCTT|ACGCTGAAAA|AACAGACAGT|AAAAACTGTC|TGCACAATGA|AGTATGACGA|180|
|TGATATGTAC|AAATGTACAC|AAGCTTGCTA|ATGTTTACCT|CTCGCTTCTA|TTTTCTGGCC|240|
|TGACGCTATG|ACCGTCCTCT|CCTCACGTAA|CGCCTTAAAA|CGCCGTACCT|GGGCGCTGTT|300|
|TATGTTCTTC|TTTTTACCCG|GACTGCTGAT|GGCCTCCTGG|GCAACCCGAA|CGCCTGCTAT|360|
|TCGGGATATT|CTTTCCGTCT|CTACCGCGGA|AATGGGGGCG|GTCTTATTCG|GGCTTTCTAT|420|
|CGGTTCAATG|AGCGGTATTC|TTTGTTCCGC|CTGGCTGGTG|AAACGATTTG|GCACCCGGAA|480|
|GGTTATTCGC|ACGACGATGA|CCTGTGCAGT|AACCGGGATG|GTTATTCTTA|GCGTCGCGCT|540|
|GTGGTGCGCC|TCGCCGCTGA|TTTTGCCCT|TGGATTAGCC|GTTTCGGCG|CCAGTTTTGG|600|
|CGCCGCCGAA|GTGGCGATTA|ATGTCGAAGG|CGCGGCGGTC|GAACGCGAGC|TGAATAAAAC|660|
|CGTTCTGCCG|ATGATGCATG|GTTTCTACAG|TTTCGGCACG|CTGGCGGGCG|CTGGTGTCGG|720|
|CATGGCGTTA|ACCGCATTAA|GCGTCCCGGC|TA| | |752|